US00PP13568P2

(12) United States Plant Patent
Trees

(10) Patent No.: US PP13,568 P2
(45) Date of Patent: Feb. 18, 2003

(54) GERANIUM PLANT NAMED 'BALCOLPURP'

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/099,259

(22) Filed: Mar. 15, 2002

(51) Int. Cl.[7] ..... A01H 5/00
(52) U.S. Cl. ..... Plt./332
(58) Field of Search ..... Plt./332

*Primary Examiner*—Kent L. Bell
(74) *Attorney, Agent, or Firm*—C. A. Whealy

(57) ABSTRACT

A new and distinct cultivar of Geranium plant named 'Balcolpurp', characterized by its cascading and mounded growth habit; freely basal branching habit; medium green-colored leaves; and purple-colored double flowers.

1 Drawing Sheet

BOTANICAL CLASSIFICATION/CULTIVAR DESIGNATION

*Pelargonium peltatum* cultivar 'Balcolpurp'.

BACKGROUND OF THE INVENTION

The present invention relates to a new and distinct cultivar of Geranium plant, botanically known as *Pelargonium peltatum,* and hereinafter referred to by the name 'Balcolpurp'.

The new Geranium is a product of a planned breeding program conducted by the Inventor in Arroyo Grande, Calif. The objective of the breeding program was to develop new freely flowering Geraniums with attractive flower and foliage colors.

The new Geranium originated from a cross-pollination made by the Inventor of the *Pelargonium peltatum* cultivar 'Chic', not patented, as the female, or seed, parent with the *Pelargonium peltatum* cultivar 'Global Bright Purple', disclosed in U.S. Plant Pat. No. 10,585, as the male, or pollen, parent. The cultivar 'Balcolpurp' was discovered and selected by the Inventor as a flowering plant within the progeny from this cross-pollination in a controlled environment in Arroyo Grande, Calif., in 1999.

Asexual reproduction of the new cultivar by terminal cuttings taken at Arroyo Grande, Calif., since June, 2000, has shown that the unique features of this new Geranium are stable and reproduced true to type in successive generations of asexual reproduction.

SUMMARY OF THE INVENTION

The following traits have been repeatedly observed and are determined to be the unique characteristics of 'Balcolpurp'. These characteristics in combination distinguish 'Balcolpurp' as a new and distinct cultivar:

1. Cascading and mounded growth habit.
2. Freely basal branching habit.
3. Medium green-colored leaves.
4. Purple-colored double flowers.

Plants of the new Geranium differ from plants of the parent cultivars primarily in flower color.

The new Geranium can be compared to the cultivar, 'Balcolav', disclosed in U.S. Plant Pat. No. 11,685. However, in side-by-side comparisons conducted in Arroyo Grande, Calif., plants of the new Geranium differed from plants of the cultivar 'Balcolav' in the following characteristics:

1. Plants of the new Geranium had shorter internodes than plants of the cultivar 'Balcolav'.
2. Plants of the new Geranium had smaller leaves than plants of the cultivar 'Balcolav'.
3. Plants of the new Geranium had smaller umbels with fewer flowers per umbel than plants of the cultivar 'Balcolav'.
4. Flowers of plants of the new Geranium had many more petals than flowers of plants of the cultivar 'Balcolav'.
5. Flower color of plants of the plants of the new Geranium was lighter than flower color of plants of the cultivar 'Balcolav'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Geranium.

The photograph at the top of the sheet comprises a side perspective view of a typical flowering plant of 'Balcolpurp'.

The photograph at the bottom of the sheet comprises a close-up view of typical flowers of 'Balcolpurp'.

DETAILED BOTANICAL DESCRIPTION

The cultivar 'Balcolpurp' has not been observed under all possible environmental conditions. The phenotype may vary somewhat with variations in environment such as temperature and light intensity, without, however, any variance in genotype. The aforementioned photographs and following observations and measurements describe plants grown 10-cm pots in Arroyo Grande, Calif., under commercial practice in a polycarbonate-covered greenhouse with day temperatures about 20 to 22° C., night temperatures about 18 to 20° C. and light levels about 2,500 to 3,000 foot-candles. Plants used for the photographs and description were about 8 to 10 weeks from planting rooted cuttings. In the following description, color references are made to The Royal Horticultural Society Colour Chart, 1995 Edition, except where general terms of ordinary dictionary significance are used.

Botanical classification: *Pelargonium peltatum* cultivar 'Balcolpurp'.

Parentage:

*Female parent.*—*Pelargonium peltatum* cultivar 'Chic', not patented.

*Male parent.*—*Pelargonium peltatum* cultivar 'Global Bright Purple', disclosed in U.S. Plant Pat. No. 10,585.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Cascading and mounded growth habit. Appropriate for 10-cm and larger containers.

*Crop time.*—Starting with a rooted cutting, about 8 to 10 weeks are required to produced a finished flowering plant in 10-cm container.

*Growth and branching habit.*—Vigorous and freely basal branching with about three lateral branches at the base. Pinching, that is, removal of terminal apices, is typically not required.

*Plant height* (*to top of foliage*).—About 16.5 cm.

*Plant width.*—About 30.7 cm.

*Lateral branches.*—Length: About 15.9 cm. Internode length: About 1.4 cm. Texture: Puberulent. Color: 146C.

*Foliage description.*—Leaves simple, generally symmetrical, abundant, opposite. Quantity of leaves per lateral branch: About ten. Length: About 3.7 cm. Width: About 5.3 cm. Shape: Reniform. Apex: Obtuse. Base: Cordate. Margin: Palmatifid. Venation pattern: Palmate. Texture, upper and lower surfaces: Leathery; glabrous. Color: Young and fully expanded foliage, upper surface: Slightly darker than 146A; venation, 144C; faint zonation, close to 187A. Young and fully expanded foliage, lower surface: 146B; venation, 144C. Petiole: Length: About 3.4 cm. Diameter: About 1.6 mm. Color: 146B.

Flower description:

*Flower arrangement and type.*—Purple-colored flowers arranged in hemispherical umbels arising from apical leaf axils. Umbels displayed above the foliage. At full flowering, usually about nine open umbels and developing umbels per plant. Flowers double and rounded in shape. Umbels persistent. Flowers not fragrant.

*Flowering season.*—Year-round under greenhouse conditions. In the garden, flowering is continuous from spring until fall.

*Umbels.*—Number of flowers per umbel: About five. Diameter: About 7.5 cm. Height: About 4.3 cm. Flower diameter: About 4.4 cm. Flower height (depth): About 1.8 cm.

*Flower buds.*—Length: About 1.7 cm. Diameter: About 1.2 cm. Shape: Ovoid. Color: Slightly darker than 66A.

*Petals/petaloids.*—Quantity: About twenty petals and about ten petaloids per flower. Petaloids variable in size and shape. Arrangement: Imbricate. Petal length: Upper petals: About 2.8 cm. Lower petals: About 2.4 cm. Petal width: Upper petals: About 1.7 cm. Lower petals: About 1.6 cm. Petal shape: Obovate. Petal/petaloid apex: Obtuse. Petal/petaloid base: Attenuate. Petal/petaloid margin: Entire. Petal/petaloid texture, upper and lower surfaces: Velvety; glabrous. Petal/petaloid color: When opening and fully opened, upper surface: Upper petals/petaloids: 80A; venation, 77A; fading to 60C with subsequent development. Lower petals/petaloids: 80A; fading to 60C with subsequent development. When opening and fully opened, lower surface: Upper petals/petaloids: 72C; venation, 67A. Lower petals/petaloids: 72C.

*Sepals.*—Quantity: About five, not imbricate. Length: About 1.2 cm. Width: About 3 mm. Shape: Ensiform to lanceolate. Apex: Acute. Margin: Entire. Texture, upper and lower surfaces: Pilose. Color, upper and lower surfaces: 146B.

*Peduncle* (*umbel stem*).—Length: About 10.1 cm. Angle: Erect. Strength: Strong. Texture: Sparse pubescence. Color: 146C slightly overlain with 178A.

*Pedicel* (*individual flower stem*).—Length: About 2 cm. Angle: Erect. Strength: Strong. Texture: Pubescent. Color: 146C.

*Reproductive organs.*—Androecium: Anther quantity: About ten. Anther length: About 2.2 mm. Anther color: Between 86A and 86B. Pollen amount: Moderate. Pollen color: 170A. Gynoecium: Pistil quantity: One. Pistil length: About 1.3 cm. Stigma shape: Five-parted, star-shaped. Stigma color: Closest to 71B. Style length: About 4 mm. Style color: Closest to 12C.

*Seed/fruit.*—Seed and fruit development has not been observed.

Disease/pest resistance: Resistance to pathogens and pests common to Pelargonium has not been observed.

It is claimed:

1. A new and distinct cultivar of Geranium plant named 'Balcolpurp', as herein illustrated and described.

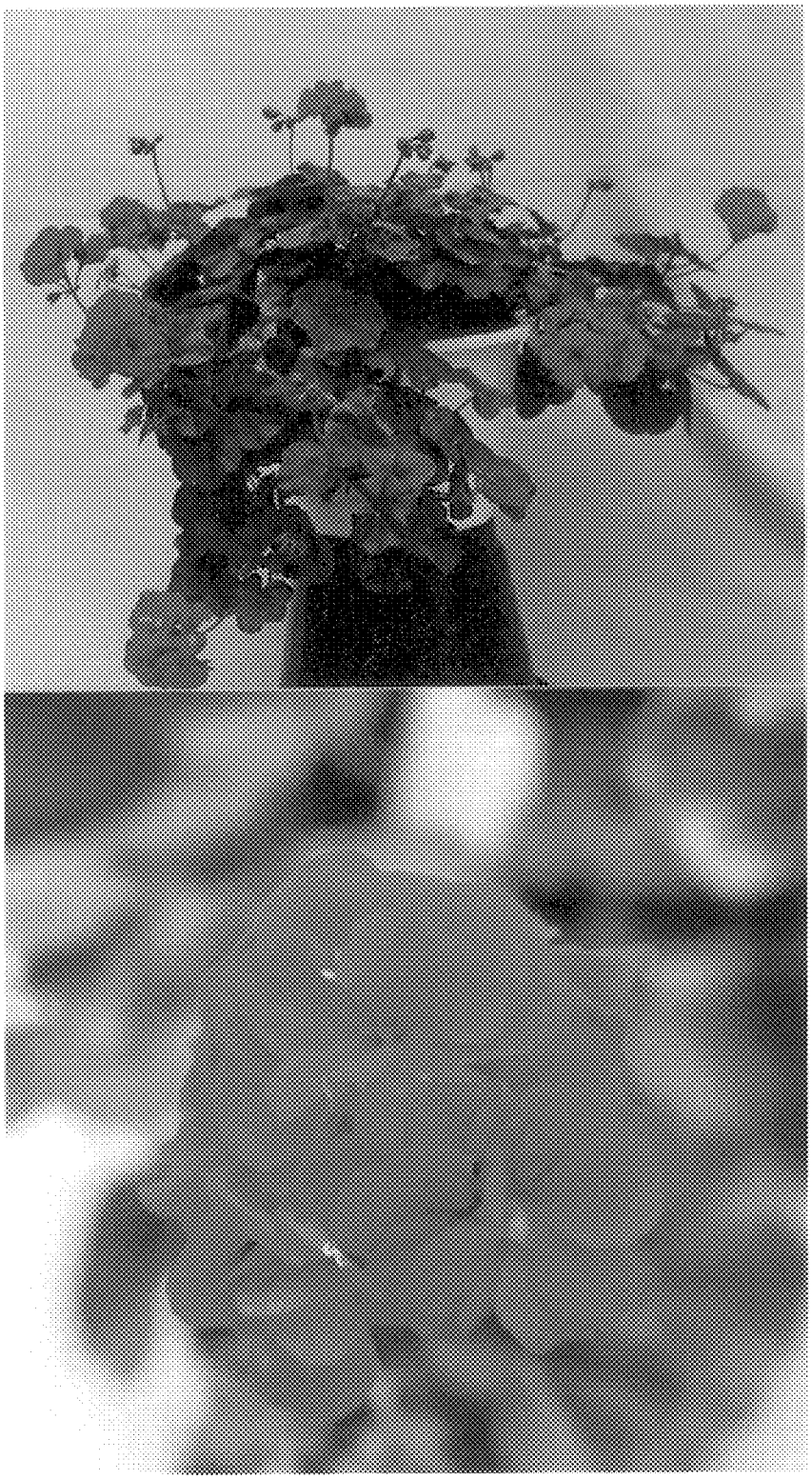

* * * * *